(12) United States Patent
Chuu et al.

(10) Patent No.: US 8,288,150 B2
(45) Date of Patent: Oct. 16, 2012

(54) METHOD FOR BREAKING THE CELL WALLS OF MICROALGAE

(75) Inventors: Jiunn-Jye Chuu, Xindian (TW); Shun-Lai Li, Tainan (TW); Hsiao-Hui Hsieh, Yongkang (TW); Chia-Hui Cheng, Rende Township, Tainan County (TW)

(73) Assignee: Analytica Bioenergy, Inc., Great Neck, NY (US)

( * ) Notice: Subject to any disclaimer, the term of this patent is extended or adjusted under 35 U.S.C. 154(b) by 287 days.

(21) Appl. No.: 12/833,128

(22) Filed: Jul. 9, 2010

(65) Prior Publication Data

US 2012/0009655 A1  Jan. 12, 2012

(51) Int. Cl.
*C12N 1/12* (2006.01)

(52) U.S. Cl. ............... 435/257.1; 435/257.2; 435/257.3; 435/257.4; 435/257.5; 435/257.6; 435/243; 435/252.1; 435/254.1

(58) Field of Classification Search ............... 435/257.1, 435/257.2, 257.3, 257.4, 257.5, 257, 243, 435/252.2, 254.2
See application file for complete search history.

(56) References Cited

U.S. PATENT DOCUMENTS 5,801,050 A * 9/1998 Uchida et al. .............. 435/257.1

OTHER PUBLICATIONS

Afi et al. Org. Geochem. (1996) 25(1/2): 117-130.*

* cited by examiner

*Primary Examiner* — Susan Hanley
(74) *Attorney, Agent, or Firm* — Alan Kamrath; Kamrath IP Lawfirm, PA

(57) ABSTRACT

A method for breaking the cell walls of microalgae includes cultivating microbes in a cultivating liquid, adding microalgae into the cultivating liquid to mix with the microbes, releasing a hydrolysis ferment from the microbes, hydrolyzing cell walls of the microalgae by the hydrolysis ferment of the microbes to decompose the cell walls of the microalgae into saccharide, and removing the microalgae from the cultivating liquid. Thus, the microbes release the hydrolysis ferment after the microalgae touch the microbes so as to hydrolyze and decompose the cell walls of the microalgae in a moderate manner without breaking the contents of the microalgae so that the contents of the microalgae can be released, absorbed and used completely.

9 Claims, 1 Drawing Sheet

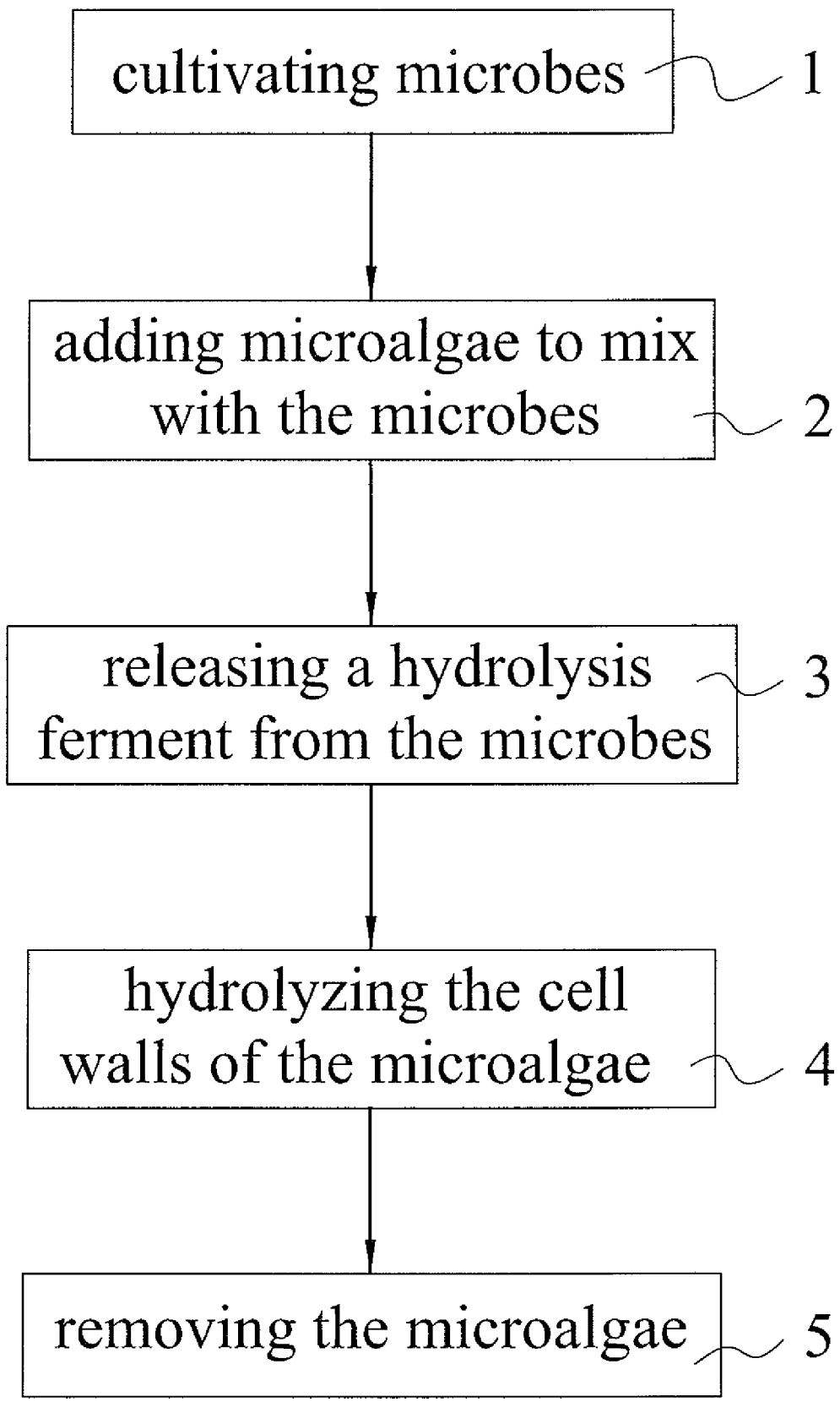

METHOD FOR BREAKING THE CELL WALLS OF MICROALGAE

BACKGROUND OF THE INVENTION

1. Field of the Invention

The present invention relates to a biological method and, more particularly, to a method for breaking the cell walls of microalgae.

2. Description of the Related Art

A conventional mechanical method for breaking cell walls of cells comprises using a grinding or cutting tool to break the cell walls of the cells. However, this method easily indirectly breaks the contents (including original liquid, fat, proteins and the like) of the cells. In addition, this method is available for animal organisms and is not available for the microbes. A conventional physical method for breaking the cell walls of cells comprises freezing and dissolving the cells reciprocally to break the cell walls of the cells. However, this method is not available for the cells of the microbes. Another conventional physical method for breaking the cell walls of cells comprises vibrating the cells by supersonic waves of a determined power to break the cell walls of the cells. However, this method easily breaks the sensitive and active features of the cells. A conventional chemical method for breaking the cell walls of cells comprises using organic solvent to change the permeability of the cell walls of the cells so that the contents of the cells can permeate the cell walls of the cells. However, this method needs a very long working time, thereby decreasing the working efficiency.

BRIEF SUMMARY OF THE INVENTION

In accordance with the present invention, there is provided a method for breaking the cell walls of microalgae, comprising a first step of cultivating microbes in a cultivating liquid, a second step of adding microalgae into the cultivating liquid to mix with the microbes, a third step of releasing a hydrolysis ferment from the microbes, a fourth step of hydrolyzing cell walls of the microalgae by the hydrolysis ferment of the microbes to decompose the cell walls of the microalgae into saccharide, and a fifth step of removing the microalgae from the cultivating liquid.

In the first step, the cultivating liquid is contained within a predetermined space, and the microbes are increased successively in the cultivating liquid within the predetermined space. In the preferred embodiment of the present invention, the microbes are fungi. In the second step, the number of the microalgae corresponds to that of the microbes so that the cell walls of the microalgae are decomposed completely by the microbes. In the third step, the microbes release the hydrolysis ferment after the microalgae are added into the cultivating liquid and touch the microbes. In the fourth step, the hydrolysis ferment of the microbes decomposes the cell walls of the microalgae to gradually form pores in the cell walls of the microalgae, and the pores in the cell walls of the microalgae are enlarged gradually during the hydrolyzing process. The microalgae have contents including fat. When the diameter of each of the pores in the cell walls of the microalgae is greater than the volume of the fat of the microalgae, the fat of the microalgae flows outward from the cell walls of the microalgae and floats upward to the top of the cultivating liquid. In the fifth step, the microalgae containing original liquid are removed from the cultivating liquid after the cell walls of the microalgae are decomposed completely. In the fifth step, the microbes have a predetermined number after the cell walls of the microalgae are decomposed completely. In the fifth step, the microalgae and the saccharide in the cultivating liquid are filtered and removed from the predetermined space.

According to the primary advantage of the present invention, the microbes release the hydrolysis ferment after the microalgae touch the microbes so as to hydrolyze and decompose the cell walls of the microalgae in a moderate manner without breaking the contents of the microalgae so that the contents of the microalgae can be released, absorbed and used completely.

According to another advantage of the present invention, the microbes still have a predetermined number after the cell walls of the microalgae are decomposed completely so that the microalgae can be added successively into the cultivating liquid to mix with the microbes so as to proceed the process of breaking the cell walls of the microalgae in a cyclic manner, thereby enhancing the working efficiency of hydrolyzing and decomposing the microalgae.

Further benefits and advantages of the present invention will become apparent after a careful reading of the detailed description with appropriate reference to the accompanying drawings.

BRIEF DESCRIPTION OF THE SEVERAL VIEWS OF THE DRAWING(S)

FIG. 1 is a flow chart of a method for breaking the cell walls of microalgae in accordance with the preferred embodiment of the present invention.

DETAILED DESCRIPTION OF THE INVENTION

Referring to FIG. 1, a method for breaking the cell walls of microalgae in accordance with the preferred embodiment of the present invention comprises a first step 1 of cultivating microbes in a cultivating liquid, a second step 2 of adding microalgae into the cultivating liquid to mix with the microbes, a third step 3 of releasing a hydrolysis ferment from the microbes, a fourth step 4 of hydrolyzing cell walls of the microalgae by the hydrolysis ferment of the microbes to decompose the cell walls of the microalgae into saccharide, and a fifth step 5 of removing the microalgae from the cultivating liquid.

In the first step 1, the cultivating liquid is contained within a predetermined space so that the microbes are increased successively in the cultivating liquid within the predetermined space. In the preferred embodiment of the present invention, the microbes are fungi, bacteria or actinomyces.

In the second step 2, the number of the microalgae corresponds to that of the microbes so that the cell walls of the microalgae are decomposed completely by the microbes. In addition, the microalgae have contents including original liquid, fat, proteins and the like.

In the third step 3, the microbes release the hydrolysis ferment after the microalgae are added into the cultivating liquid and touch the microbes. In the preferred embodiment of the present invention, the hydrolysis ferment is a fibrin or cellulose that can decompose the cell walls of the microalgae.

In the fourth step 4, the hydrolysis ferment of the microbes decomposes the cell walls of the microalgae to gradually form pores in the cell walls of the microalgae, and the pores in the cell walls of the microalgae are enlarged gradually during the hydrolyzing process. Thus, when the diameter of each of the pores in the cell walls of the microalgae is greater than the volume of the fat of the microalgae, the fat of the microalgae flows outward from the cell walls of the microalgae and floats upward to the top of the cultivating liquid. Then, the fat of the microalgae is removed from the cultivating liquid.

In the fifth step 5, the microalgae containing the original liquid are removed from the cultivating liquid after the cell walls of the microalgae are decomposed completely. At this time, the microbes still have a predetermined number after the cell walls of the microalgae are decomposed completely. In addition, the microalgae and the saccharide in the cultivating liquid are filtered and removed from the predetermined space.

In practice, the microbes are placed into and cultivated in the cultivating liquid within the predetermined space so that so that the microbes are increased successively in the cultivating liquid within the predetermined space. After the microbes are increased to have a predetermined number, the microalgae are placed into the cultivating liquid to mix with the microbes. Then, the microbes release the hydrolysis ferment after the microalgae are added into the cultivating liquid and touch the microbes so as to hydrolyze and decompose the cell walls of the microalgae into the saccharide. At the same time, the hydrolysis ferment of the microbes decomposes the cell walls of the microalgae to gradually form the pores in the cell walls of the microalgae. Then, the pores in the cell walls of the microalgae are enlarged gradually during the hydrolyzing process. Thus, when the diameter of the pores in the cell walls of the microalgae is greater than the volume of the fat of the microalgae, the fat of the microalgae flows outward from the cell walls of the microalgae and floats upward to the top of the cultivating liquid. Then, the fat of the microalgae is removed from the cultivating liquid. At this time, the operator can observe the color of the microalgae in the cultivating liquid to see if the cell walls of the microalgae have been decomposed completely. Then, the microalgae and the saccharide in the cultivating liquid are filtered and removed after the cell walls of the microalgae are decomposed completely so that the microalgae containing the original liquid are removed from the cultivating liquid. Thus, a cycle of breaking the cell walls of the microalgae is accomplished. At this time, the microbes still have a predetermined number after the cell walls of the microalgae are decomposed completely so that other microalgae can be added into the cultivating liquid to mix with the microbes so as to proceed another cycle of breaking the cell walls of the microalgae. In such a manner, the fat of the microalgae can be used to make bio-diesel fuel, the saccharide converted by the cell walls of the microalgae can be used as a health food or feedstuff, and the residues of the microalgae can be used as a fertilizer.

Accordingly, the microbes release the hydrolysis ferment after the microalgae touch the microbes so as to hydrolyze and decompose the cell walls of the microalgae in a moderate manner without breaking the contents of the microalgae so that the contents of the microalgae can be released, absorbed and used completely. In addition, the microbes still have a predetermined number after the cell walls of the microalgae are decomposed completely so that the microalgae can be added successively into the cultivating liquid to mix with the microbes so as to proceed the process of breaking the cell walls of the microalgae in a cyclic manner, thereby enhancing the working efficiency of hydrolyzing and decomposing the microalgae.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the true scope of the invention.

The invention claimed is:

1. A method for breaking the cell walls of microalgae, comprising:
   a first step of cultivating microbes in a cultivating liquid;
   a second step of adding microalgae into the cultivating liquid to mix with the microbes;
   a third step of releasing a hydrolysis ferment from the microbes;
   a fourth step of hydrolyzing cell walls of the microalgae by the hydrolysis ferment of the microbes to decompose the cell walls of the microalgae into saccharide; and
   a fifth step of removing the resultant cell-wall hydrolyzed microalgae from the cultivating liquid.

2. The method for breaking the cell walls of microalgae of claim 1, wherein in the first step, the cultivating liquid is contained within a predetermined space, and the microbes are increased successively in the cultivating liquid within the predetermined space.

3. The method for breaking the cell walls of microalgae of claim 1, wherein the microbes are fungi.

4. The method for breaking the cell walls of microalgae of claim 1, wherein in the second step, the number of the microalgae corresponds to that of the microbes so that the cell walls of the microalgae are decomposed completely by the microbes.

5. The method for breaking the cell walls of microalgae of claim 1, wherein in the third step, the microbes release the hydrolysis ferment after the microalgae are added into the cultivating liquid and touch the microbes.

6. The method for breaking the cell walls of microalgae of claim 1, wherein in the fourth step, the hydrolysis ferment of the microbes decomposes the cell walls of the microalgae to gradually form pores in the cell walls of the microalgae, and the pores in the cell walls of the microalgae are enlarged gradually during the hydrolyzing process.

7. The method for breaking the cell walls of microalgae of claim 1, wherein
   the microalgae have contents including fat;
   when the diameter of each pore in the cell walls of the microalgae is greater than the volume of the fat of the microalgae, the fat of the microalgae flows outward from the cell walls of the microalgae and floats upward to the top of the cultivating liquid.

8. The method for breaking the cell walls of microalgae of claim 1, wherein in the fifth step, the microbes have a predetermined number after the cell walls of the microalgae are decomposed completely.

9. The method for breaking the cell walls of microalgae of claim 1, wherein in the fifth step, the resultant cell-wall hydrolyzed microalgae and the saccharide are removed from the cultivating liquid by filtration.

* * * * *